(12) United States Patent
Gomi et al.

(10) Patent No.: US 10,856,793 B2
(45) Date of Patent: Dec. 8, 2020

(54) WHEEL FRAME OF DRIVING WHEEL OF A WHEEL CHAIR INCLUDING AN ERGOMETER INCLUDING IMPROVED STABILIZATION FOR INCREASING TORQUE MEASUREMENT OF A USER

(71) Applicant: HONDA MOTOR CO., LTD., Tokyo (JP)

(72) Inventors: Hiroshi Gomi, Saitama (JP); Yoshinao Sodeyama, Saitama (JP); Junji Takado, Saitama (JP); Hiroshi Uematsu, Saitama (JP); Toru Takenaka, Saitama (JP)

(73) Assignee: HONDA MOTOR CO., LTD., Tokyo (JP)

( * ) Notice: Subject to any disclaimer, the term of this patent is extended or adjusted under 35 U.S.C. 154(b) by 181 days.

(21) Appl. No.: 16/092,913

(22) PCT Filed: Mar. 29, 2017

(86) PCT No.: PCT/JP2017/013037
§ 371 (c)(1),
(2) Date: Oct. 11, 2018

(87) PCT Pub. No.: WO2018/025443
PCT Pub. Date: Feb. 8, 2018

(65) Prior Publication Data
US 2019/0083023 A1      Mar. 21, 2019

(30) Foreign Application Priority Data
Aug. 2, 2016   (JP) .................................. 2016-151895

(51) Int. Cl.
*G01L 5/16* (2020.01)
*A61B 5/22* (2006.01)
(Continued)

(52) U.S. Cl.
CPC ................ *A61B 5/221* (2013.01); *A61G 5/02* (2013.01); *A61G 5/026* (2013.01); *A61G 5/10* (2013.01);
(Continued)

(58) Field of Classification Search
None
See application file for complete search history.

(56) References Cited

U.S. PATENT DOCUMENTS

| 5,649,883 A | 7/1997 | Mayes et al. |
| 6,113,519 A | 9/2000 | Goto |
| 2007/0173392 A1 | 7/2007 | Stanford |

FOREIGN PATENT DOCUMENTS

| FR | 2960421 A1 | 12/2011 |
| JP | 58-177649 A | 10/1983 |

(Continued)

OTHER PUBLICATIONS

International Search Report dated Jul. 4, 2017, issued in counterpart application No. PCT/JP2017/013037 (4 pages).
(Continued)

*Primary Examiner* — Harshad R Patel
*Assistant Examiner* — Nigel H Plumb
(74) *Attorney, Agent, or Firm* — Westerman, Hattori, Daniels & Adrian, LLP

(57) ABSTRACT

A wheel frame (16*a*) includes a cylindrical hub (16*c*) into which an axle (11*b*) is rotatably inserted, a six-axis force sensor (16*e*) having an insertion hole (16*e*1) into which the hub (16*c*) is inserted, and an outer flange (16*f*) extending radially outward from an input section (16*e*2) of the six-axis force sensor (16*e*), wherein a hand rim (17) is attached to the outer flange (16*f*).

16 Claims, 6 Drawing Sheets

(51) Int. Cl.
*A61G 5/02* (2006.01)
*A61G 5/10* (2006.01)
*A63B 22/20* (2006.01)
*A63B 22/06* (2006.01)
*A63B 71/00* (2006.01)
*B60B 1/00* (2006.01)
*B60B 27/00* (2006.01)

(52) U.S. Cl.
CPC ............ *A61G 5/1054* (2016.11); *A63B 22/06* (2013.01); *A63B 22/20* (2013.01); *A63B 71/0009* (2013.01); *B60B 1/006* (2013.01); *B60B 27/0068* (2013.01); *G01L 5/16* (2013.01); *A61G 5/1051* (2016.11); *A61G 2203/30* (2013.01); *A61G 2203/32* (2013.01); *A63B 2022/0635* (2013.01); *A63B 2071/0018* (2013.01)

(56) References Cited

FOREIGN PATENT DOCUMENTS

| | | |
|---|---|---|
| JP | 9-19460 A | 1/1997 |
| JP | 9-84898 A | 3/1997 |
| JP | 11-299834 A | 11/1999 |
| JP | 2002-224169 A | 8/2002 |
| JP | 2013-192875 A | 9/2013 |

OTHER PUBLICATIONS

Partial supplementary European Search Report dated May 23, 2019, issued in counterpart EP Application No. 17836550.8. (10 pages).

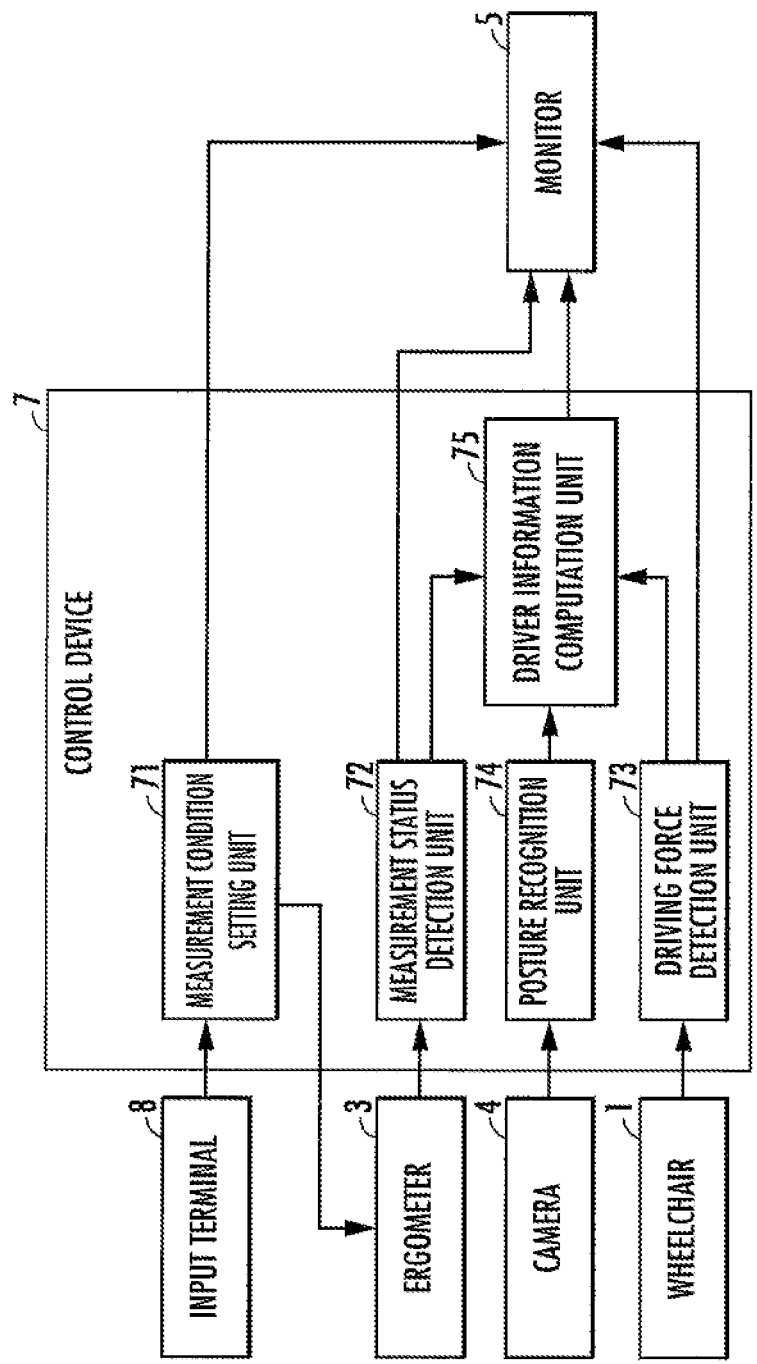

WHEEL FRAME OF DRIVING WHEEL OF A WHEEL CHAIR INCLUDING AN ERGOMETER INCLUDING IMPROVED STABILIZATION FOR INCREASING TORQUE MEASUREMENT OF A USER

TECHNICAL FIELD

The present invention relates to a wheel frame of a driving wheel of a wheelchair used in measuring a motion of a driver, a driving wheel using the wheel frame, a wheelchair using the driving wheel, an ergometer suitable for measurement using the wheelchair, and a measurement system using the wheelchair and the ergometer.

BACKGROUND ART

A traditionally known wheelchair includes a strain gauge installed on each of a plurality of support members supporting a hand rim on a wheel surface in order to measure a driving force applied by a driver to the wheelchair via the hand rim (a force applied to the hand rim when operating the wheel chair) (for example, refer to Patent Literature 1).

Also, when measurement is to be carried out on a wheelchair used in track races, marathons, and the like, a wheelchair as described in Patent Literature 1 and an ergometer are sometimes used in combination.

A known ergometer of this type includes a pair of rollers arranged to contact corresponding one of a pair of driving wheels of a wheelchair and adapted to rotate with the rotation of the driving wheels, a detector adapted to detect a torque, a rotation speed, and the like of the rollers, and a motor adapted to apply driving and braking forces to the rollers.

CITATION LIST

Patent Literature

Patent Literature 1: Japanese Patent Application Laid-Open No. 2013-192875

SUMMARY OF INVENTION

Technical Problem

However, since a strain gauge is used as the detector in the conventional wheelchair driving wheels described in Patent Literature 1, the magnitude of the driving force can be measured but the direction and the like of the force cannot be measured in detail.

In view of this, another approach is to use a six-axis force sensor that can also measure the direction of the force in detail as the detector instead of a strain gauge. However, when six-axis force sensors that are generally used are installed for each of a plurality of support members supporting the hand rim, the size of the driving wheels increases in both the axial direction and the radial direction, resulting in considerable increase in its weight as well.

Also, when using multiple six-axis force sensors, the force (hexaxial force) acting on the wheel flame from the hand rim is detected as the resultant force of those of all the six-axis force sensors. However, this resultant force is easily affected by an internal force applied to the wheel frame (e.g., an internal force generated by deformation of the wheel frame due to road surface reaction force and the like). Accordingly, if measurement is performed using multiple six-axis force sensors, a problem arises that the detection precision is degraded unless characteristics of the individual six-axis force sensors are strictly in agreement with each other.

Also, as the weight of the driving wheel increases, the moment of inertia generated at the driving wheel will have a magnitude that cannot be ignored in the measurement. Accordingly, when the measurement is performed by reproducing the measurement status using an ergometer configured to correspond to a wheelchair of a general weight, the problem arises that the reproducibility is degraded due to the influence of the moment of inertia and precise measurement cannot be performed.

It is therefore an object of the present invention, which has been made in view of the above aspects, to provide a wheel frame capable of measuring the magnitude and direction of driving force in detail while suppressing increase in weight and size of a driving wheel, a driving wheel using the same wheel frame, a wheelchair using the same driving wheel, an ergometer suitable for measurement using the same wheelchair, and a measurement system using the same wheelchair and the same ergometer.

Solution to Problem

In order to achieve the above object, the wheel frame according to the present invention is a wheel frame of a driving wheel of a wheelchair, the wheel frame including a cylindrical hub into which an axle extending from a cage of the wheelchair is inserted, wherein the cylindrical hub is rotatably attached to the axle, a six-axis force sensor having an insertion hole into which the hub is inserted, and a first support member to which a hand rim of the wheelchair is attached, the first support member extending outward in a radial direction from a load input section of the six-axis force sensor.

As described above, since the wheel frame of the present invention measures the force applied to the hand rim (i.e., the driving force) using the six-axis force sensor, the driving force can be detected as six-component forces (the individual forces in three orthogonal axial directions plus the moments about the individual axes).

Also, since the hand rim is connected via the first support member in this wheel frame, it is made possible to detect, by one single six-axis force sensor, any force applied to any location on the hand rim. By suppressing the required number of six-axis force sensors in this way, increase in weight is suppressed in the driving wheel configured using this wheel frame.

In addition, since one six-axis force sensor is used, this wheel flame is less susceptible to the influence of an internal force even when the internal force is generated in the wheel frame due to deformation of the wheel frame caused by the road surface reaction force or the like when compared with a case where multiple six-axis force sensors are used. As a result, degradation of the detection accuracy is suppressed.

Further, this wheel frame is configured such that the hub is inserted into the insertion hole of the six-axis force sensor. Specifically, the six-axis force sensor is arranged at a proximate portion of the hub where the thickness of the wheel frame is largest (i.e., the center portion in the radial direction of the wheel flame). Accordingly, the size in the axial direction of the driving wheel configured using this wheel frame does not increase in size as a result of arranging the six-axis force sensor.

As such, according to the wheel frame of the present invention, it is made possible to measure the magnitude and the direction of the driving force in detail while suppressing increase in the weight and size of the driving wheel configured by using this wheel flame.

Also, it is preferable that the wheelchair wheel of the present invention further includes a second support member extending outward in a radial direction from the hub, the first support member is attached to a radially inward portion of the six-axis force sensor, and the second support member is attached to a radially outward portion of the six-axis force sensor.

With this configuration, it is made possible to concentrate the load input section of the six-axis force sensor in the vicinity of the radial center of the wheel frame. As a result, it is made possible to further suppress the influence of the moment of inertia applied to the load input section, so that the magnitude and direction of the driving force can be measured in further detail.

Further, in the wheelchair wheel frame of the present invention configured to include the second support member, it is preferable that the second support member has an annular rim section an outer peripheral surface there being fitted with a tire.

In this manner, it is made possible to further suppress increase in the weight by integrating the second support member for supporting the six-axis force sensor and the member for fitting the tire with each other.

Also, it is preferable in the wheel for the wheelchair according to the present invention that it further includes a second support member extending outward in the radial direction from an end of the hub, the end being proximal to the cage, the six-axis force sensor is inserted via an other end of the hub, the other end being opposite to the end of the hub proximal to the cage, an inner diameter of the insertion hole of the six-axis force sensor is of a size allowing creation of a predetermined gap from an outer peripheral surface of the hub when the hub is inserted, the first support member has a first mounting section projecting in a direction toward the cage, the second support member has a second mounting section projecting in a direction opposite to the direction toward the cage, and the six-axis force sensor is attached to the first support member via the first mounting section and attached to the second support member via the second mounting section.

With this configuration, since the contact of the six-axis force sensor other than the mounting sections of the first support member and the second support member can be suppressed, the contact portion between the six-axis force sensor and other components can be suppressed and minimized. This prevents the force other than the force of the driver input via the hand rim from being input to the six-axis force sensor and reduces the noise, so that the magnitude and direction of the driving force can be measured in further detail.

Also, it is preferable in the wheel for the wheelchair according to the present invention that the insertion hole of the six-axis force sensor is a through hole extending through the six-axis force sensor, and that a length in an axial direction of the six-axis force sensor is formed to be shorter than a length in an axial direction of the hub.

With this configuration, the six-axis force sensor can be housed inside the wheel in the axial direction. As a result, it is made possible to further prevent the driving wheel from becoming larger in the axial direction. In addition, it is made possible to prevent contact of the six-axis force sensor with the driver or the cage.

Also, it is preferable in the wheel for the wheelchair according to the present invention that it further includes a second support member extending outward in a radial direction from the hub and a transmitter configured to transmit a result of detection by the six-axis force sensor to a receiver wirelessly connected thereto, the second support member is thinned in an axial direction, and the transmitter is arranged at a thinned portion of the second support member.

With this configuration, since the transmitter can be arranged inside the wheel frame, it is made possible to prevent the driving wheel from becoming large in the axial direction as a result of arranging the transmitter. Also, the signal transmitted from the transmitter is less likely to be disturbed by the components of the wheel frame. As a result, the detection accuracy is improved, so that the magnitude and direction of the driving force can be measured in more detail.

Also, in order to achieve the above object, a driving wheel according to the present invention includes any one of the above-described wheel frames.

As described above, according to the driving wheel of the present invention, since any one of the above-described wheel frames is used to configure the driving wheel, it is made possible to suppress increase in the weight and the size of the driving wheel and measure the magnitude and the direction of the driving force in detail.

Also, in order to achieve the above object, a wheelchair according to the present invention includes the above-described driving wheel.

As described above, according to the wheelchair of the present invention, since the above-described driving wheels are included, it is made possible to measure in detail the magnitude and direction of the driving force while suppressing increase in the weight and size of the driving wheel and accordingly the wheelchair as a whole.

Also, in order to achieve the above object, an ergometer according to the present invention includes a roller arranged to contact a driving wheel of a wheelchair and configured to rotate with a rotation of the driving wheel, a detector configured to detect a rotational state of the roller, a motor configured to impart a driving or braking force to the roller, and a flywheel connected to the roller, and the flywheel is configured to generate a moment of inertia in a direction in which an influence due to a weight acting on the roller is reduced.

As described above, the ergometer of the present invention includes the flywheel connected to the roller. The flywheel generates a moment of inertia in a direction in which the influence of the weight applied to the roller is reduced.

Specifically, the moment of inertia of the flywheel is specified such that the moment of inertia generated about the axis of the driving wheel when the driving wheel is driven on the ergometer is in agreement with the moment of inertia generated about the axis of the driving wheel when running the usual wheelchair that does not include a detector on a real road surface (hereinafter referred to as "actual running").

More specifically, the moment of inertia of the flywheel is specified such that a value obtained by equivalently converting the moment of inertia of the entire device including the flywheel into the moment of inertia about the axis of the driving wheel of the wheelchair at the time of the measurement is in agreement with a sum of the value obtained by equivalently converting the mass of the vehicle body and the driver into the moment of inertia about the driving wheel of the wheelchair, a value obtained by equivalently converting the moment of inertia of the wheel(s) other than the driving wheel of the wheelchair into the moment of inertia about the axis of the driving wheel, and a value of the moment of inertia of the driving wheel of the wheelchair at the time of actual running.

By virtue of this, the influence of the weight from the driving wheel acting on the roller can be offset and suppressed by the flywheel even when a wheelchair has a heavier driving wheel than a driving wheel used in actual running of a wheelchair which is a measurement target (e.g., a driving wheel that includes with any one of the above-described wheel frames).

As such, according to the ergometer of the present invention, even if the wheelchair has a heavy weight of the driving wheels as in the above wheelchair, the influence by the weight is suppressed and accurate measurement can be performed.

Also, in the ergometer according to the present invention, it is preferable that the flywheel is a variable flywheel allowing the moment of inertia to be changed.

With this configuration, accurate measurement can be performed for wheelchairs and drivers of various weights.

Also, in order to achieve the above object, an ergometer according to the present invention includes a roller arranged to contact a driving wheel of a wheelchair and configured to rotate with a rotation of the driving wheel, a detector configured to detect a rotational state of the roller, a motor configured to impart a driving or braking force to the roller, and a replaceable flywheel connected to the roller, and the flywheel is one flywheel selected from a plurality of flywheels having different moments of inertia in a direction in which an influence due to a weight acting on the roller is reduced.

Thus, the ergometer of the present invention includes the flywheel connected to the roller. The flywheel generates a moment of inertia in a direction in which the influence of the weight applied to the roller is reduced.

As a result, even if a driving wheel heavier than the driving wheel used in the actual running of the wheelchair to be measured (e.g., the one using the above-described wheel frame) is used, the influence of the weight applied to the roller from the driving wheel can be offset and suppressed by the flywheel.

In addition, since a plurality of flywheels having different moments of inertia to be generated are included and a flywheel to be arranged between the roller and the motor is selected from among the flywheels, the measurement can be performed on wheelchairs of various weights.

Accordingly, according to the ergometer of the present invention, even if multiple wheelchairs having driving wheels of heavy weights, such as the wheelchair described above, are influenced by their weights, the influence of the weights can be suppressed and accurate measurement can be performed.

Also, the measurement system according to the present invention includes the above-described wheelchair, any one of the above-described ergometer, a posture detector configured to detect a posture of a driver of the wheelchair, and a computation device, and the computation device is configured to estimate a joint torque or a muscular strength of the driver based on detection information from the six-axis force sensor of the wheelchair, detection information from the detector of the ergometer, and detection information from the posture detector.

As described above, the joint torque or muscle force of a driver can be precisely estimated by performing measurement using the above-described wheelchair and ergometer while simultaneously using the posture detector.

BRIEF DESCRIPTION OF DRAWINGS

FIG. 6 is a block diagram of a control device of the measurement system of FIG. 1.

DESCRIPTION OF EMBODIMENTS

A measurement system S according to an embodiment will be described hereinbelow with reference to the drawings. While the measurement system S performs measurements on a wheelchair 1 used in track racing, marathon, and the like, the measurement system according to the present invention is also capable of performing measurements on wheelchairs other than the wheelchairs for competition.

Figure 1:
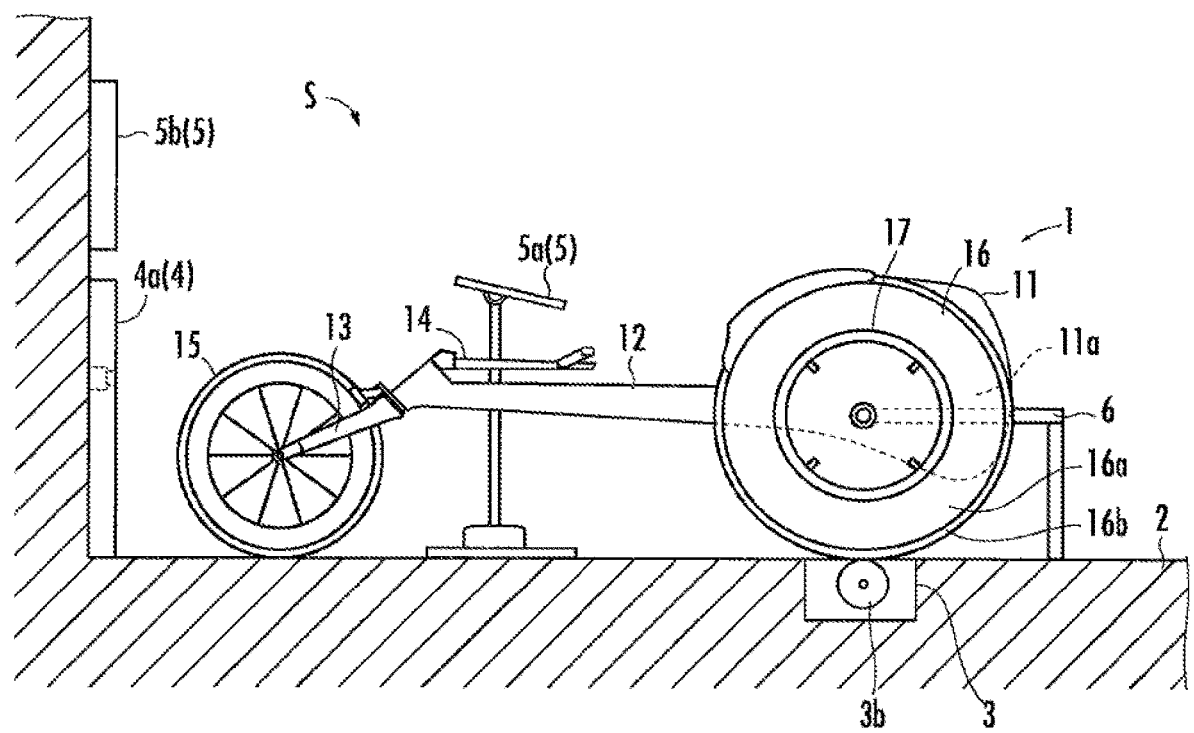
FIG. 1 is a side view illustrating a schematic configuration of a measurement system according to an embodiment.
Figure 2:
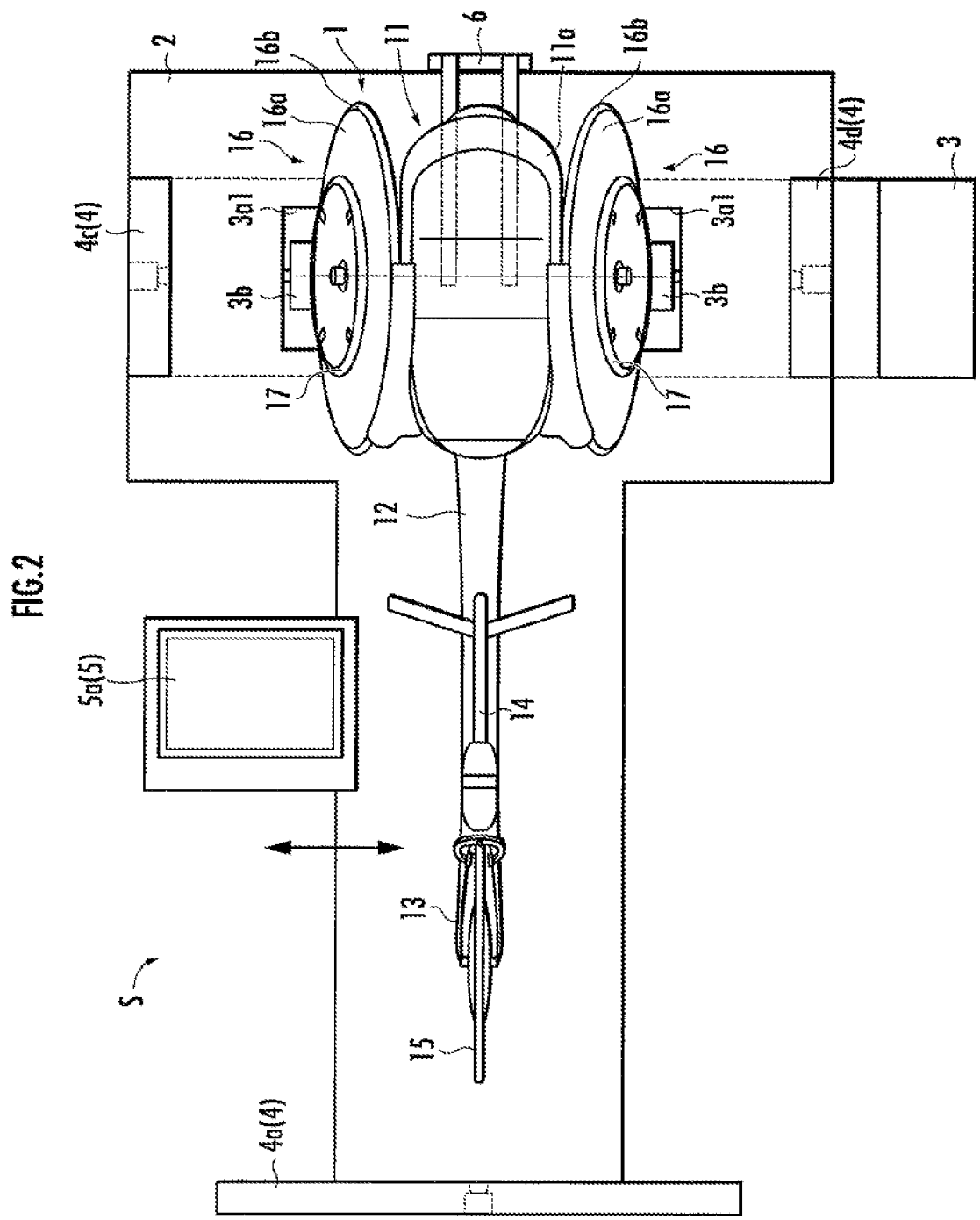
FIG. 2 is a plan view of the measurement system of FIG. 1.

As illustrated in FIGS. 1 and 2, the measurement system S includes a casing 2 on which the wheelchair 1 is placed; an ergometer 3 built in the casing 2; four cameras 4 ("posture detector") for photographing a posture of a driver of the wheelchair 1, two monitors 5, which are display devices for allowing the driver to recognize data such as measurement results; a fixing member 6 for fixing the position of the wheelchair 1, a control device 7, which is not shown in FIG. 1 (see FIG. 6); and an input terminal 8, which is not shown in FIG. 1 (see FIG. 6).

As illustrated in FIG. 1, the wheelchair 1 includes a cage 11, a vehicle body frame 12 extending in the front side of the cage 11, a front fork 13 pivotally supported at a front end portion of the vehicle body frame 12, a steering handlebar 14 attached to a rear end portion of the front fork 13, a front wheel 15 held at a front end portion of the front fork 13, a pair of rear wheels 16 ("driving wheel") attached to the left and right of the cage 11, and a pair of hand rims 17 each attached to corresponding one of the rear wheels 16 at an opposite side thereof with respect to the cage 11.

As illustrated in FIG. 2, an upper portion of the cage 11 is open, and a seating seat 11a on which the driver is seated is arranged inside the cage 11.

The front fork 13 is pivotally supported at a distal end portion of the vehicle body frame 12 so as to be rotatable. The handlebar 14 is attached to the rear end portion of the front fork 13. The front wheel 15 is rotatably held at the front end portion of the front fork 13. As a result, the wheelchair 1 is configured such that operation of the handlebar 14 causes the direction of the front wheel 15 to be changed via the front fork 13 so that the wheelchair 1 can be turned in a desired direction.

The rear wheel 16 is constituted by a wheel frame 16a and a tire 16b fitted to the wheel frame 16a. The rear wheel 16 is rotatably attached to the cage 11 via the axle 11b (see FIG. 4) extending in the left-right direction of the cage 11 in a state where the rear wheel 16 is inclined such that the upper portion of the rear wheel 16 becomes closer to the center portion of the cage 11.

Each of the hand rims 17 is fixed to the corresponding one of the rear wheels 16 so as to be integrally rotatable with the corresponding one of the rear wheels 16. As a result, the wheelchair 1 is configured such that the driver can transmit the driving force to the rear wheel 16 via the hand rim 17 so as to run the wheelchair 1.

Here, the rear wheels 16 will be described in detail with reference to FIGS. 3 and 4.

The rear wheels 16 are each constituted by a wheel frame 16a and a tire 16b (not shown in FIGS. 3 and 4) fitted to the wheel frame 16a.

Figure 3:
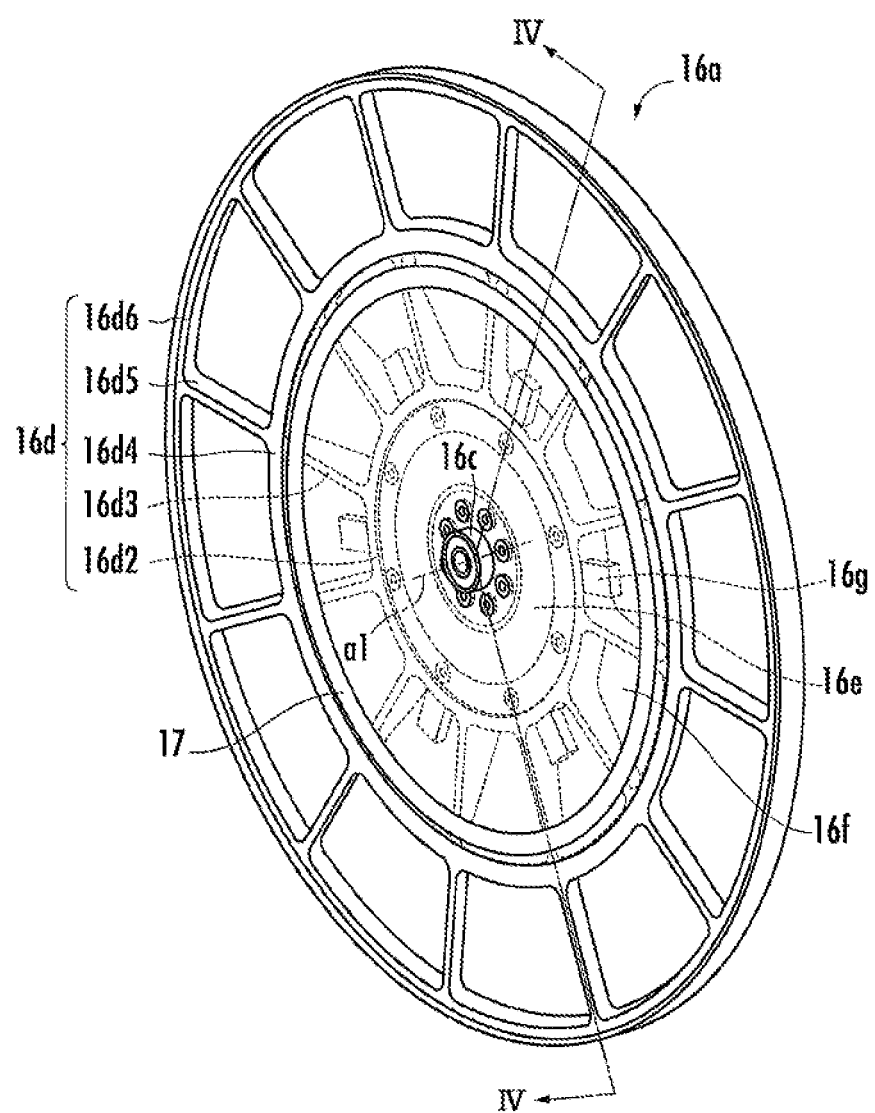
FIG. 3 is a perspective view of a wheel frame of a driving wheel of a wheelchair of the measurement system of FIG. 1.
Figure 4:
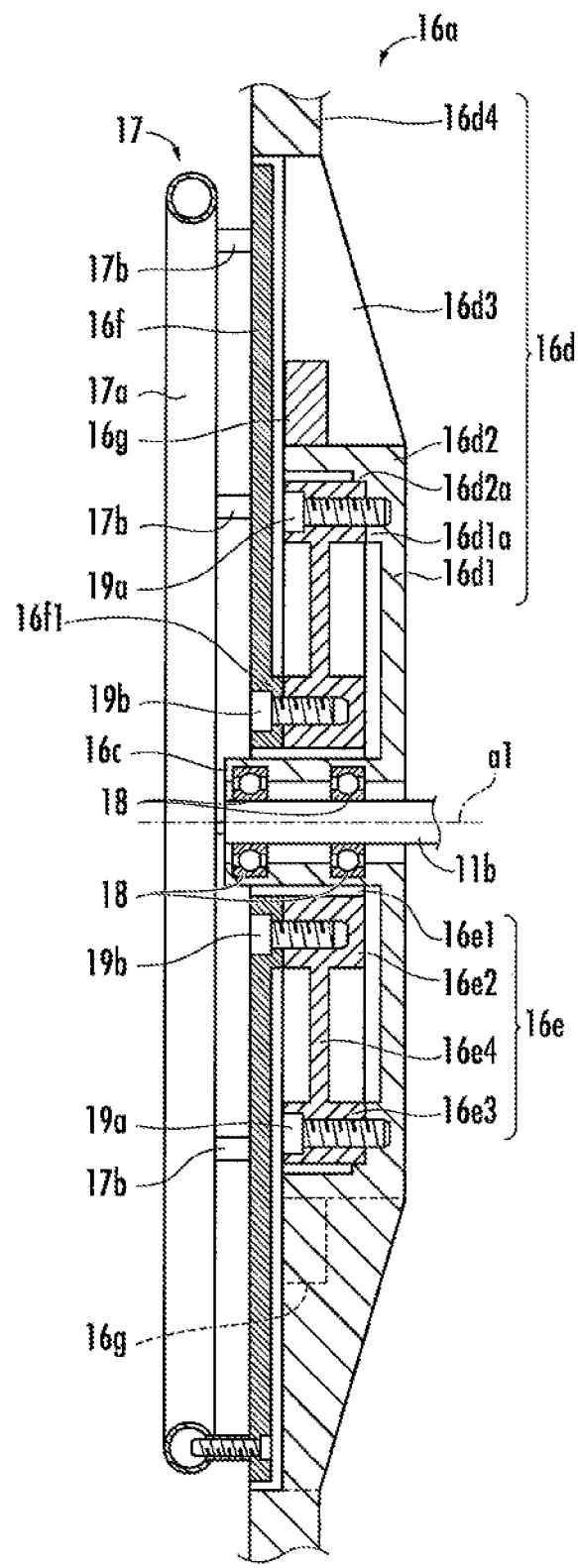
FIG. 4 is an enlarged cross-sectional view taken along the line IV-IV of the main part of the wheel frame of FIG. 3.

The wheel flame 16a includes, as illustrated in FIGS. 3 and 4, a tubular hub 16c, an inner flange 16d ("second support member") which is a wheel frame body portion that extends radially from an end of the hub 16e on the proximal side with respect to the cage 11, an annular six-axis force sensor 16e into which the hub 16e is inserted, and an outer flange 16f ("first support member") which is an annular cover configured to cover an area from the vicinity of the hub 16e to the vicinity of the hand rim 17 on the surface of the wheel frame 16a on the opposite side with respect to the cage 11, and a plurality of transmitters 16g arranged at a thinned portion of the inner flange 16d.

Although not shown in FIGS. 3 and 4, the rear wheel 16 also includes a cover that covers the portion on the surface of the wheel frame 16a opposite to the cage 11, the portion extending from the region in the vicinity of the hand rim 17 to the peripheral portion on the outer side in the radial direction.

The hub 16c is a cylindrical member as illustrated in FIG. 4. The axle 11b extending from the cage 11 of the wheelchair 1 is inserted into the hub 16c. As a result, the hub 16c (and accordingly the entire wheel frame 16a) is rotatable about the rotational axis line a1 of the axle 11b via a bearing 18.

The inner flange 16d includes, as illustrated in FIGS. 3 and 4, in an order with reference to the hub 16e (inner peripheral side), a disk-shaped disk section 16d1 connected to the hub 16c, a cylindrical first rim section 16d2, a plurality of rod-shaped first rib sections 16d3 extending radially, a second annular rim section 16d4, a plurality of rod-shaped second rib sections 16d5 extending radially, and a third annular rim 16d6, where the tire 16b is fitted to the outer peripheral surface of the third annular rim 16d6.

The disk section 16d1 is formed in a disk shape extending radially outward from the outer peripheral surface of the hub 16c and reaching a position beyond the outer peripheral portion of the six-axis force sensor 16e. A first projecting section 16d1a ("second mounting section") protruding toward the side away from the cage 11 is formed on the outer peripheral portion of the disk section 16d1.

The annular six-axis force sensor 16e is attached to the first projecting section 16d1a with a plurality of first mounting screws 19a on the surface on the proximal side with respect to the cage 11 at the portion radially outward thereof (more specifically, a mounting section 16e3 which will be described later). As a result, a gap is formed between the surface of the six-axis force sensor 16e on the proximal side with respect to the cage 11 and the disk section 16d1 of the inner flange 16d except for portion where the first projecting section 16d1a is provided.

The first rim section 16d2 is formed in a tubular shape extending in the axial direction along the outer peripheral surface of the six-axis force sensor 16e from the end portion on the outer peripheral side of the disk section 16d1. In the first rim section 16d2, a second projecting section 16d2a protruding inward is formed in the inner peripheral surface of the end portion on the side of the cage 11 (that is, in the vicinity of the connecting portion for connection with the disk section 16d1).

The annular six-axis force sensor 16e is in contact with the second projecting section 16d2a only at the outer peripheral surface of the end portion on the side of the cage 11. As a result, between the six-axis force sensor 16e and the first rim section 16d2 of the inner flange 16d, a gap is formed in a portion other than the portion where the second projecting section 16d2a is provided.

The first rib section 16d3 is formed as a plurality of rod-like members extending radially outward in the radial direction from the outer peripheral surface of the first rim section 16d2. Since the first rib section 16d3 is formed as a rod-like member, the inner flange 16d is formed in a shape thinned in the axial direction between the first rim section 16d2 and the second rim section 16d4.

Also, the surface of the first rib section 16d3 on the side of the cage 11 is inclined away from the cage 11 so as to become thinner in the axial direction as the surface extends outward in the radial direction. As a result, the wheel frame 16a as a whole is made thinner radially outward.

The second rib section 16d5 is formed as a plurality of rod-like members extending radially outward in the radial direction from the outer peripheral surface of the second rim section 16d4. Since the second rib section 16d5 is formed as a rod-like member, the inner flange 16d is formed in a shape thinned in the axial direction between the second rim section 16d4 and the third rim section 16d6.

As illustrated in FIGS. 3 and 4, the six-axis force sensor 16e is a disk-shaped member at the center portion of which an insertion hole 16e1 is formed, and its thickness is defined to be thinner than the length in the axial direction of the hub 16c. The six-axis force sensor 16e includes an input section 16e2 (load input section) on the inner peripheral side thereof; a mounting section 16e3 on the outer peripheral side thereof, and a detection section 16e4 between the input section 16e2 and the mounting section 16e3.

The insertion hole 16e1 is formed as a through hole. The hub 16c is inserted into and passed through the insertion hole 16e1 from the side of the cage 11. Also, the inner diameter of the insertion hole 16e1 is sufficiently larger than the outer diameter of the hub 16c. As a result, when the six-axis force sensor 16e is attached to the inner flange 16d, a predetermined interval is created between the inner peripheral surface of the insertion hole 16e1 and the outer peripheral surface of the hub 16c.

The insertion hole 16e1 in the six-axis force sensor 16e is formed as a through hole, and the thickness of the six-axis force sensor 16e is thinner than the length in the axial direction of the hub 16c. As a result, the six-axis force sensor 16e does not protrude from the inner flange 16d in the axial direction but remains in a state where it is accommodated in the wheel frame 16a.

The input section 16e2 is a portion provided inward in the radial direction of the six-axis force sensor 16e. The outer flange 16f is attached to the surface of the input section 16e2 on the side opposite to the side of the cage 11 by a plurality of second mounting screws 19b.

The mounting section 16e3 is a portion of the six-axis force sensor 16e provided outward in the radial direction. The mounting section 16e3 is attached to the inner flange 16d by the plurality of first mounting screws 19a on the surface proximal with respect to the cage 11.

As described above, in the six-axis force sensor 16e, the input section 16e2 to which the outer flange 16f for attaching the hand rim 17 is attached is provided inward in the radial direction of the six-axis force sensor 16e and the mounting section 16e3 for attaching the six-axis force sensor 16e to the inner flange 16d is provided outward in the radial direction of the six-axis force sensor 16e.

In other words, in the six-axis force sensor 16e, the input section 16e2 which is the load input section is concentrated in the vicinity of the center in the radial direction of the wheel flame 16a. By virtue of this, in the six-axis force sensor 16e, the influence of the moment of inertia applied to the input section 16e2 is suppressed.

The detection section 16e4 is provided between the input section 16e2 and the mounting section 16e3. The detection section 16e4 is formed of a material having lower rigidity than the material of the input section 16e2 and the mounting section 16e3, and a strain gauge is provided. The strain gauge is designed to be distorted in accordance with the force input from the hand rim 17 via the outer flange 16f and the input section 16e2.

As described above, in the six-axis force sensor 16e, the input section 16e2 and the mounting section 16e3 used for attachment are formed of a material having sufficiently high rigidity as compared with the detection section 16e4 which is a section for detection. This prevents deformation of the input section 16e2 and the mounting section 16e3, stabilizes the force transmitted to the detection section 16e4, and thereby improves the detection accuracy.

As illustrated in FIGS. 3 and 4, the outer flange 16f is configured as a disk-shaped member that covers portions from the hub 16c to the inside of the second rim section 16d4 of the inner flange 16d.

A third projecting section 16f1 ("first mounting section") protruding toward the cage 11 side is formed on the radially inward peripheral edge portion of the outer flange 16f.

The annular six-axis force sensor 16e is attached to the third projecting section 16f1 on the surface on the side opposite to the cage 11 of the radially inward portion thereof (specifically, the input section 16e2) by a plurality of second mounting screw 19b. As a result, a gap is created between the surface of the six-axis force sensor 16e on the side opposite to the cage 11 and the outer flange 16f except for the portion where the third projecting section 16f1 is provided.

A handle rim body section 17a of the hand rim 17 is fixed to the outer peripheral portion of the outer flange 16f via a plurality of support members 17b.

In this manner, the outer flange 16f extends radially outward from the input section 16e2 of the six-axis force sensor 16e (i.e., toward the hand rim 17). As a result, the force (i.e., the driving force) applied to the hand rim 17 is input to the input section 16e2 of the six-axis force sensor 16e via the outer flange 16f.

The transmitter 16g wirelessly transmits the detection result of the six-axis force sensor 16e toward a not-shown receiver. As illustrated in FIGS. 3 and 4, the transmitter 16g is arranged in a thinned portion defined by the first rim section 16d2, the first rib section 16d3, and the second rim section 16d4 of the inner flange 16d.

In this manner, since the transmitter 16g is arranged in the thinned portion of the inner flange 16d, the wheel frame 16a is not enlarged in the axial direction due to the arrangement of the transmitter 16g. In addition, the signal transmitted from the transmitter 16g is less likely to be disturbed by the components of the wheel frame 16a.

As described above, since the driving force is measured by the six-axis force sensor 16e in the wheel frame 16a of the rear wheel 16 of the wheelchair 1 of the measurement system S, the driving force can be detected as six component forces (the individual force of three orthogonal axial directions plus the individual moments about the respective axes).

In addition, since the hand rim 17 is connected via the outer flange 16f, it is made possible to detect any force acting upon any location on the hand rim 17 using one six-axis force sensor 16e. By suppressing the necessary number of six-axis force sensors 16e in this manner, increase in weight is suppressed in the rear wheel 16 configured using this wheel frame 16a.

In addition, since one six-axis force sensor 16e is used in this wheel frame 16a, even if the wheel frame 16a is deformed due to the road surface reaction force or the like and an internal force is generated, it is less susceptible to the influence of the internal force compared with the case of using a plurality of six-axis force sensors. As a result of this, reduction in detection accuracy is suppressed.

In addition, in the wheel frame 16a, the hub 16c is inserted into the insertion hole 16e1 of the six-axis force sensor 16e. In other words, a six-axis force sensor 16e having a smaller thickness in the axial direction than the length in the axial direction of the hub 16c is arranged in the vicinity of the hub 16e where the thickness of the wheel fame 16a is the thickest (that is, the central portion in the radial direction of the wheel flame 16a). As a result, the size in the axial direction of the rear wheel 16 configured by using the wheel frame 16a does not increase in size due to arrangement of the six-axis force sensor 16e.

Further, in the wheel fame 16a, a gap is created between the hub 16c and the inner flange 16d on the inner peripheral side, the outer peripheral side, and the cage side of the six-axis force sensor 16e. That is, the six-axis force sensor 16e is in contact with only the first projecting section 16d1a and the second projecting section 16d2a of the inner flange 16d and the third projecting section 16f1 of the outer flange 16f.

As a result of this, a contact portion between the six-axis force sensor 16e and other components is minimized, and forces other than the force of the driver input via the hand rim 17 is prevented from being input to the six-axis force sensor 16e, and the noise is reduced.

Accordingly, in the rear wheel 16, which is configured using the wheel frame 16a and accordingly the wheelchair 1 including the rear wheel 16, it is made possible to suppress increase in the weight and the size, and the magnitude and the direction of the driving force can be measured in detail.

Note that the wheel frame of the rear wheel 16 of the wheelchair 1 that can be applied to the measurement system S is not limited to the wheel frame 16a configured as described above.

In the above-mentioned wheel frame 16a, an annular six-axis force sensor is used as the six-axis force sensor 16e. However, any other six-axis force sensor may be used as long as it includes at the center portion thereof an insertion hole into which the hub can be inserted.

For example, in the wheel frame 16a, the insertion hole 16e1 of the six-axis force sensor 16e is formed as a through hole, but the insertion hole may not be a through hole as long as the axle of the wheelchair can be inserted into it. Meanwhile, in the case of an insertion hole not being formed as a through hole, the size in the axial direction of the wheelchair having the driving wheel constituted by using the wheel frame will be increased unless the axle is shortened or any other appropriate measure is taken as compared with a wheelchair including driving wheels configured by using the one having the insertion hole in the form of a through hole.

Further, in the wheel flame 16a, a strain gauge type sensor is used as the six-axis force sensor 16e, but any other type may be used as long as it can detect the six component forces of the input force. For example, a capacitance type six-axis force sensor may be used.

Also, in the wheel frame 16a, gaps are created between the hub 16c and the inner flange 16d on the inner peripheral side, the outer peripheral side, and the cage side of the six-axis force sensor 16e. However, it is not always necessary to provide all of these gaps, and the number or positions thereof may be appropriately modified.

For example, in a case where a wheel flame is formed of a material capable of sufficiently absorbing vibrations, the projecting section may not be formed and the gap may not be created. In addition, in a case where a portion where the component member is not in contact with the six-axis force sensor is formed (for example, when the first rim section 16d2 is not extended along the outer periphery of the six-axis force sensor 16e) or the like, the gap with respect to the component member that is not in contact will be automatically omitted.

Also, in order to suppress the influence of the moment of inertia of the wheel frame 16a, the hand rim 17 is attached to the radially inward portion of the six-axis force sensor 16e via the outer flange 16f which is the first support member. In other words, the load input portion is a radially inward portion. However, the mounting position of the first support member is not limited to the radially inward portion of the six-axis force sensor.

For example, if the magnitude of the generated moment of inertia is sufficiently small, the first support member may be attached to the radially outer portion of the six-axis force sensor. In other words, the load input portion may be a radially outer portion.

Also, in the wheel frame 16a, the input section 16e2 and the mounting section 16e3 of the six-axis force sensor 16e are formed of a highly rigid material, and the detection section 16e4 is made of a material having low rigidity. However, the input section, the mounting section, and the detection section of the six-axis force sensor 16e may all be made of the same material.

Note that, when each part of the six-axis force sensor is formed of the same material as mentioned above, the detection accuracy can be improved in the same or similar manner as in the case where the parts are formed of materials of different rigidity such that the strain generated in the detection section, for example, by making the detection section thin both in its thickness and width becomes larger than the strain generated in any other part.

Further, in the wheel frame 16a, the outer flange 16f which is the first support member is formed as a single disk. However, as long as the shape of the first support member is such that the input section of the six-axis force sensor and the hand rim can be connected to each other, the shape of the first support member may be appropriately modified according to the required weight and rigidity.

For example, it may be formed such that it has a disk-shaped disk section and an outer peripheral portion on the rib by cutting out the portion on the outer peripheral side. In the case of such a shape, the signal transmitted from the transmitter 16g is not easily disturbed by the first support member, so that more accurate measurement can be performed.

Further, in the wheel frame 16a, the inner flange 16d which is the second support member is formed of a disk-shaped disk section 16d1 and three concentric rims (a first rim section 16d2, a second rim section 16d4, and a third rim section 16d6) having different diameters and a plurality of rod-like ribs (a first rib section 16d3 and a second rib section 16d5) radially arranged between the rims. However, the shape of the second support member may be appropriately modified according to the required weight and rigidity.

For example, the shapes of the rims and the ribs, the number of the ribs, etc. may be modified or it may be formed as a single disk.

Also, in the wheel frame 16a, the six-axis force sensor 16e is attached to the hub 16c via the inner flange 16d which is the second support member. However, in the case where the six-axis force sensor is directly attached to the hub and the rib or the rim is provided directly on the outer periphery of the six-axis force sensor, the second support member may be omitted.

Further, in the wheel frame 16a, a transmitter 16g that wirelessly transmits a signal to the receiver is arranged in the thinned portion of the inner flange 16d. However, the configuration and position of the transmitter are not limited to this configuration. For example, a wired transmitter may be used, and its arrangement position may be modified as appropriate.

Next, the ergometer 3 will be described in detail with reference to FIGS. 1, 2, and 5.

As illustrated in FIGS. 1 and 2, as the basic configuration of the ergometer 3, the ergometer 3 is arranged at a position below the placement position of the wheelchair 1 so as to be fitted in the casing 2 of the measurement system S.

Figure 5:
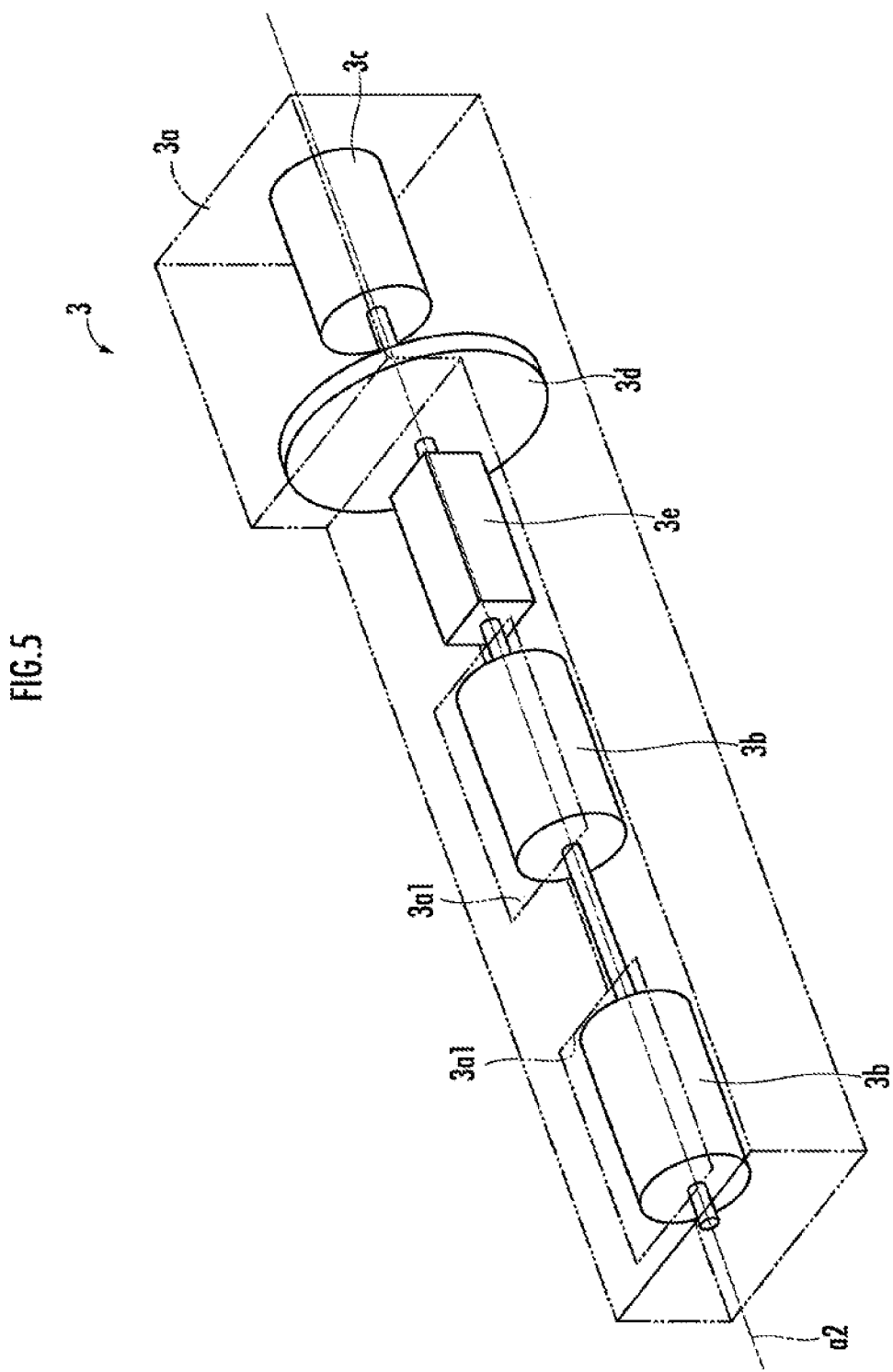
FIG. 5 is a perspective view illustrating a configuration of an ergometer of the measurement system of FIG. 1.

As illustrated in FIG. 5, a pair of rollers 3b, which are arranged so as to be in contact with corresponding one of the rear wheels 16 of the wheelchair 1 to be measured, a motor 3e arranged on the rotation axis line a2 of the roller 3b; a flywheel 3d arranged between the roller 3b and the motor 3c; and a torque meter 3e (detector) arranged between the roller 3b and the flywheel 3d are arranged inside the ergometer casing 3a of the ergometer 3 (see FIG. 2).

On the upper surface of the ergometer casing 3a, two openings 3a1 are formed at positions below the rear wheel 16 when the wheelchair 1 is placed. The rollers 3b are individually exposed via corresponding one of the two openings 3a1.

The roller 3b rotates with the rotation of the rear wheel 16 in contact therewith. The rotational state (torque, rotational speed, etc.) of the roller 3b is detected by a torque meter 3e equipped with a rotational speed detector and transmitted to the control device 7.

Also, driving and braking forces are applied to the roller 3b from the motor 3c via the flywheel 3d. The driving and braking forces applied to the roller 3b (i.e., the output torque of the motor 3c) are controlled by a signal from the control device 7.

Specifically, the output torque of the motor 3c is controlled so as to simulatively generate the running resistance corresponding to the actual running of the rear wheel 16 in contact with the roller 3b. More specifically, the output torque of the motor 3c is controlled such that the load torque generated when trying to maintain the speed of the rear wheel 16, which is the driving wheel, at the time of measurement using the ergometer 3 is in agreement with the load torque generated in actual running at the same speed.

In the ergometer 3, by controlling the driving and braking forces of the roller 3b with the motor 3c in this manner, it is made possible to apply the same load as that in the actual running to the arm of the driver.

The flywheel 3d generates a moment of inertia in a direction resulting in the reduction of the influence of the weight applied by the roller 3b. The flywheel 3d is a variable flywheel capable of changing the generated moment of inertia by changing the built-in additional mass based on a signal from the control device 7.

The moment of inertia of the flywheel 3d is controlled such that the moment of inertia generated about the axis of the axle 11b when the rear wheel 16 is driven on the ergometer 3 is in agreement with the moment of inertia generated about the axis of the axle 11b in actual running of the wheelchair 1.

More specifically, the moment of inertia of the flywheel 3d is controlled such that a value obtained by equivalently converting the moment of inertia of the entire wheelchair 1 including the flywheel 3d at the time of measurement into the moment of inertia about the axis of the axle 11b is brought into agreement with a sum of a value obtained by equivalently converting the mass of the wheelchair 1 and the driver at the time of actual running into the moment of inertia about the axis of the axle 11b and the value obtained by equivalently converting the moment of inertia of the front wheel 15 into the moment of inertia about the axis of the axle 11b, and the value of the moment of inertia of the rear wheel 16.

This allows the influence of the weight to be offset and suppressed by the flywheel 3d even when wheelchairs and drivers of various weights are to be measured, such as a wheelchair having a heavier driving wheels than the driving wheels used in actual traveling (more specifically, the wheelchair 1 including the above-mentioned rear wheel 16).

Accordingly, the ergometer 3 suppresses the influence of weight even when the wheelchair 1 having the heavy rear wheels 16 is to be measured, so that accurate measurement can be performed.

Note that the ergometer applicable to the measurement system S is not limited to the ergometer 3 configured as described above.

The above-described ergometer 3 is configured such that, by using a variable flywheel as the flywheel 3d, the magnitude of the moment of inertia generated for offsetting the influence of the weight in accordance with the weight of the wheelchair can be modified. However, any flywheel may be used as long as it can accommodate itself to the weight to be offset.

For example, the ergometer 3 may be configured such that the flywheel can be replaced, a plurality of flywheels generating different moments of inertia are prepared, and the one that generates an appropriate moment of inertia may be selected from among the flywheels.

Also, when the weight of the wheelchair to be measured is fixed, only the flywheel that generates the moment of inertia suitable for this weight may be incorporated in the ergometer in place of the variable flywheel or the flywheel that can be selectably replaced.

Further, the ergometer 3 uses the torque meter 3e as the detector for measuring the torque, the rotational speed, and the like of the roller 3b. However, the detector may be appropriately modified in accordance with the parameters to be measured.

In addition, in the ergometer 3, the flywheel 3d and the torque meter 3e which is the detector are arranged between the roller 3b and the motor 3c. However, it suffices that the flywheel is connected to the roller 3b, and any detector may be used as long as it is capable of detecting the rotation state of the roller 3b. As a result, the arrangement positions of the flywheel and the detector may be appropriately changed in accordance with the size of the ergometer as a whole and the like.

Also, the ergometer 3 includes the pair of rollers 3b provided so as to contact corresponding one of the rear wheels 16. However, any roller may be used as long as it is capable of applying a load to the driving wheel, and only one roller may be provided for the pair of driving wheels.

Next, the camera 4 will be described with reference to FIGS. 1 and 2.

The measurement system S has a first camera 4a for photographing the driver from the front, a second camera 4b for photographing the driver from above, a third camera 4c for photographing the driver from the right side, and a fourth camera 4d for photographing the driver from the left side as the camera 4 for detecting the posture of the driver aboard the wheelchair 1.

The measurement system S, by means of these cameras 4, photographs the driver having signs attached to various parts of the body, and computes the positions of the driver's neck, shoulder, hip, and elbow at each time by the control device 7 on the basis of the photographed moving images or the successively photographed still images.

Next, the monitor 5 will be described with reference to FIGS. 1 and 2.

In the measurement system S, has, as a monitor 5 for a driver riding on the wheelchair 1 to check his/her status during the measurement, a first monitor 5a that is slidable and movable to a position below the drivers face at the time of operation and a second monitor 5b fixed to the front side of the wheelchair 1.

The posture of the driver that has been detected; the driving force computed by the control device 7; and the joint torques, the muscular strength, and the like of the driver are displayed on the first monitor 5a and the second monitor 5b in addition to the measurement conditions of the ergometer 3 that have been specified and the measurement statuses such as the torque and the rotation speed of the roller 3b of the ergometer 3.

Next, the fixing member 6 will be described with reference to FIGS. 1 and 2.

In the measurement system S, in order to fix the relative positions of the wheelchair 1 and the casing 2 with respect to each other (more specifically, the relative positions of the wheelchair 1 and the ergometer 3), a fixing member 6 capable of fixing the position of the cage 11 of the wheelchair 1 is provided in the rear of the casing 2.

Note that the fixing member 6 is not limited to the above-described configuration, and a fixing member for fixing the position of the front wheel 15 of the wheelchair 1 may be provided, or fixing members for fixing the front wheel and fixing members for fixing the rear wheels may be used in combination.

Next, the control device 7 will be described with reference to FIG. 6.

The control device 7 has functionality as a calculation device and a database. The control device 7 is configured by one or a plurality of electronic circuit units including a CPU, a RAM unit, a ROM unit, an HDD, an interface circuit, and the like.

As illustrated in FIG. 6, the control device 7 includes, as functions realized by the implemented hardware configuration or program, a measurement condition setting unit 71 configured to set the measurement conditions, a measurement status detection unit 72 configured for recognizing the status of the ergometer 3, a driving force detection unit 73 configured to detect the driving force when the driver operates the wheelchair 1, a posture recognition unit 74 configured to recognize the posture of the driver, and a driver information estimation unit 75 configured to estimate the joint torques and the muscle force of the driver.

The measurement condition setting unit 71 is configured to recognize the measurement conditions on the basis of the signal input from the input terminal 8 and changes the torque applied to the roller 3b from the motor 3c of the ergometer 3 and the moment of inertia of the flywheel 3d on the basis of the recognized signal. As a result, a load similar to that when the vehicle actually runs is applied to the arm of the driver of the wheelchair 1.

The measurement status detection unit 72 is configured to detect a signal from the detector of the ergometer 3 and recognize the current measurement status on the basis of the detection signal and the signal from the measurement condition setting unit 71.

The driving force detection unit 73 is configured to detect, at each point in time, the driving force applied by the driver to the wheelchair 1 on the basis of the detection signal of the driving force applied to the wheelchair 1 (the force applied by the driver to the hand rim 17 when operating the wheelchair 1) (i.e., the detection signal of the six-axis force sensor 16e).

The posture recognition unit 74 recognizes the posture of the driver (more specifically, the sign attached to various parts of the driver's body) on the basis of the information on the image photographed by the camera 4, and computes and recognizes the driver's neck, shoulder, hip, and elbow positions at each point in time.

The driver information estimation unit 75 estimates the joint torques of the driver in the respective measurement statuses on the basis of the measurement statuses detected by the measurement status detection unit 72, the driving force applied to the wheelchair 1 detected by the driving force detection unit 73 and the posture of the driver recognized by the posture recognition unit 74, and computes the muscular strength of the driver on the basis of the joint torques.

As described above, since the measurement system S uses the wheelchair 1 and the ergometer 3 as described above, it simulatively reproduces various statuses and can accurately measure the driving force of the wheelchair 1 by the driver in these statuses. And the joint torques and the muscle forces of the driver can be precisely estimated.

It should be noted that the computation device applicable to the measurement system S is not limited to the control device 7 configured as described above. Although the above-mentioned control device 7 controls the state of the ergometer 3 by the measurement condition setting unit 71, it may be omitted if the ergometer 3 can independently specify the measurement conditions.

REFERENCE SIGNS LIST

1: wheelchair; 2: casing; 3: ergometer; 3a: ergometer casing; 3a1: opening; 3b: roller; 3c: motor; 3d: flywheel; 3e: torque meter (detector); 4: camera (posture detector); 4a: first camera; 4b: second camera; 4c: third camera; 4d: fourth camera; 5: monitor; 5a: first monitor; 5b: second monitor 6: fixing member; 7: control device (computation device); 8: input terminal; 11: cage; 11a: seating seat; 11b: axle; 12: vehicle body frame; 13: front fork 14: steering handlebar; 15: front wheel; 16: rear wheel (driving wheel); 16a: wheel frame; 16b: tire; 16c: hub; 16d: inner flange (second support member); 16d1: disk section; 16d1a: first projecting section (second mounting section); 16d2: first rim section; 16d2a: second projecting section; 16d3: first rib section; 16d4: second rim section; 16d5: second rib section; 16e: six-axis force sensor; 16e1: insertion hole; 16e2: input section (load input section); 16e3: mounting section; 16e4: detection section; 16f: outer flange (first support member); 16f2: third projecting section (first mounting section); 16g transmitter; 17: hand rim; 17a: hand rim body section; 17b: support member; 18: bearing; 19a: first mounting screw; 19b: second mounting screw; 71: measurement condition setting unit; 72: measurement status detection unit; 73: driving force detection unit; 74: posture recognition unit; 75: driver information estimation unit; a1: first axis line; a2: second axis line; S: measurement system.

The invention claimed is:

1. A wheel frame for a driving wheel of a wheelchair, the wheel frame comprising:
   a cylindrical hub into which an axle extending from a cage of the wheelchair is inserted, wherein the cylindrical hub is rotatably attached to the axle;
   a six-axis force sensor having an insertion hole into which the hub is inserted; and
   a first support member to which a hand rim of the wheelchair is attached, the first support member extending outward in a radial direction from a load input section of the six-axis force sensor.

2. The wheel frame according to claim 1, further comprising a second support member extending outward in a radial direction from the hub, wherein
   the first support member is attached to a radially inward portion of the six-axis force sensor, and
   the second support member is attached to a radially outward portion of the six-axis force sensor.

3. The wheel frame according to claim 2, wherein the second support member has an annular rim section on an outer peripheral surface thereof being fitted with a tire.

4. The wheel frame according to claim 1, further comprising a second support member extending outward in the radial direction from an end of the hub, the end being proximal to the cage, wherein
   the six-axis force sensor is inserted via an other end of the hub, the other end being opposite to the end of the hub proximal to the cage,
   an inner diameter of the insertion hole of the six-axis force sensor is of a size allowing creation of a predetermined gap from an outer peripheral surface of the hub when the hub is inserted,
   the first support member has a first mounting section projecting in a direction toward the cage,
   the second support member has a second mounting section projecting in a direction opposite to the direction toward the cage, and
   the six-axis force sensor is attached to the first support member via the first mounting section, and attached to the second support member via the second mounting section.

5. The wheel frame according to claim 1, wherein
   the insertion hole of the six-axis force sensor is a through hole extending through the six-axis force sensor, and
   a length in an axial direction of the six-axis force sensor is formed to be shorter than a length in an axial direction of the hub.

6. The wheel frame according to claim 1, further comprising:
   a second support member extending outward in a radial direction from the hub; and
   a transmitter configured to transmit a result of detection by the six-axis force sensor to a receiver wirelessly connected thereto, wherein
   the second support member is thinned in an axial direction, and the transmitter is arranged at a thinned portion of the second support member.

7. A driving wheel comprising the wheel frame according to claim 1.

8. A wheelchair comprising the driving wheel according to claim 7.

9. A measurement system comprising:
a wheel-type moving vehicle including a wheel;
an ergometer;
a posture detector configured to detect a posture of a driver of the wheel-type moving vehicle; and
a computation device, wherein
the wheel including a hand rim configured to transmit a driving force input from the driver to an axle of the wheel and a six-axis force sensor configured to detect a multiaxial force applied to the axle,
the ergometer including a roller arranged to contact the wheel of the wheel-type moving vehicle and configured to rotate with a rotation of the wheel, and a rotation detector configured to detect a rotational state of the roller, and
the computation device being configured to estimate a joint torque or a muscular strength of the driver based on detection information from the six-axis force sensor of the wheel-type moving vehicle, detection information from the rotation detector of the ergometer, and detection information from the posture detector.

10. The measurement system according to claim 9, wherein
the wheel-type moving vehicle is a wheelchair,
the wheel is a driving wheel,
a wheel frame of the driving wheel includes:
a cylindrical hub into which the axle extending from a cage of the wheelchair is inserted, the cylindrical hub being rotatably attached to the axle;
the six-axis force sensor having an insertion hole into which the hub is inserted; and
a first support member to which the hand rim is attached, the hand rim being a hand rim of the wheelchair, the first support member extending outward in a radial direction from a load input section of the six-axis force sensor.

11. The measurement system according to claim 9, wherein the ergometer includes a motor configured to impart driving or braking force to the roller, and a flywheel connected to the roller, the flywheel being configured to generate a moment of inertia in a direction in which an influence due to a weight acting on the roller is reduced.

12. The measurement system according to claim 9, further comprising:
a measurement condition setting unit configured to set a measurement condition;
a measurement status detection unit configured to recognize a status of the ergometer;
a driving force detection unit configured to detect the driving force input by the driver to the wheel-type moving vehicle;
a posture recognition unit configured to recognize the posture of the driver; and
a driver information estimation unit configured to estimate the joint torque or the muscular strength of the driver.

13. The measurement system according to claim 9, further comprising a monitor configured to display at least one of a measurement condition of the ergometer, a measurement status of the ergometer, the posture of the driver, a magnitude of the input by the driver, the joint torque of the driver, and the muscular strength of the driver.

14. The measurement system according to claim 13, wherein the monitor includes a first monitor arranged at a position below a face of the driver when the driver is aboard the wheel-type moving vehicle and a second monitor arranged at a front side of the wheel-type moving vehicle.

15. The measurement system according to claim 9, wherein the posture detector includes a camera configured to photograph the driver and a posture computation unit configured to calculate the posture of the driver based on an image captured by the camera.

16. The measurement system according to claim 9, wherein the rotation detector is a torquemeter configured to measure at least either of a torque and a rotation speed of the roller.

* * * * *